United States Patent
Stivland (10) Patent No.: US 8,465,456 B2
(45) Date of Patent: Jun. 18, 2013

(54) EXTENDABLE ASPIRATION CATHETER

(75) Inventor: Timothy Stivland, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 11 days.

(21) Appl. No.: 12/183,388

(22) Filed: Jul. 31, 2008

(65) Prior Publication Data

US 2010/0030186 A1 Feb. 4, 2010

(51) Int. Cl.
*A61M 5/178* (2006.01)

(52) U.S. Cl.
USPC .............. 604/164.01; 604/103.04; 604/96.01; 604/104; 604/105; 604/106

(58) Field of Classification Search
USPC .............. 604/104–109, 96.01, 103.04, 164.01
See application file for complete search history.

(56) References Cited

U.S. PATENT DOCUMENTS

| | | | |
|---|---|---|---|
| 3,631,848 A | 1/1972 | Muller | |
| 3,687,142 A | 8/1972 | Leibinzohn | |
| 4,690,131 A | 9/1987 | Lyddy, Jr. et al. | |
| 5,324,263 A * | 6/1994 | Kraus et al. | 604/96.01 |
| 5,637,102 A * | 6/1997 | Tolkoff et al. | 604/536 |
| 5,749,858 A | 5/1998 | Cramer | |
| 5,843,051 A | 12/1998 | Adams et al. | |
| 5,961,526 A | 10/1999 | Chu et al. | |
| 6,159,195 A * | 12/2000 | Ha et al. | 604/500 |
| 6,312,406 B1 * | 11/2001 | Jayaraman | 604/102.01 |
| 6,383,206 B1 * | 5/2002 | Gillick et al. | 606/200 |
| 6,544,279 B1 * | 4/2003 | Hopkins et al. | 606/200 |
| 6,632,230 B2 | 10/2003 | Barry | |
| 6,638,268 B2 | 10/2003 | Niazi | |
| 6,969,381 B2 | 11/2005 | Voorhees | |
| 7,316,678 B2 * | 1/2008 | Nash et al. | 604/528 |
| 2003/0050662 A1 | 3/2003 | Don Michael | |
| 2003/0120208 A1 * | 6/2003 | Houser et al. | 604/103.04 |
| 2004/0087971 A1 * | 5/2004 | Arnott | 606/127 |
| 2004/0193046 A1 | 9/2004 | Nash et al. | |
| 2005/0085842 A1 * | 4/2005 | Eversull et al. | 606/191 |
| 2005/0119686 A1 * | 6/2005 | Clubb | 606/200 |
| 2008/0058650 A1 | 3/2008 | Saadat et al. | |
| 2008/0108946 A1 | 5/2008 | Nash et al. | |
| 2008/0125744 A1 | 5/2008 | Treacy | |
| 2008/0228258 A1 | 9/2008 | Gerdts et al. | |

* cited by examiner

*Primary Examiner* — Kevin C Sirmons
*Assistant Examiner* — Edelmira Bosques
(74) *Attorney, Agent, or Firm* — Seager, Tufte & Wickhem LLC (57) ABSTRACT

An intravascular aspirating assembly comprising an elongate guidewire having a proximally facing filter disposed on a distal portion thereof, a single operator exchange aspiration catheter disposed on the guidewire, the aspiration catheter having a proximal end, a distal end and an aspiration lumen extending therebetween, an extension catheter slidably disposed in the aspiration lumen and having a length greater than that of the aspiration catheter.

32 Claims, 10 Drawing Sheets

EXTENDABLE ASPIRATION CATHETER

FIELD OF THE INVENTION

This invention pertains generally to percutaneous intravascular devices and techniques for removing embolic debris from a blood vessel lumen and more specifically to aspiration devices and methods for removing embolic debris collected or held by another therapeutic device.

BACKGROUND

Aspiration catheters have become common tools for use with embolic protection filters and angioplasty and stent placement catheter during intravascular interventional procedures. One challenge when using embolic protection filters is that the filters can become occluded due to overloading. This prevents the embolic filters from working, as flow is needed to bring particles into the filter, and creates visibility issues when radiopaque dye cannot flow through the vessel. It is also frequently desired to remove trapped emboli from embolic filters and from around occlusion balloons prior to removing these interventional tools so as to reduce the chance of any embolic debris from flowing downstream from the interventional site.

Aspiration is a potential method of removing these embolic particles from within filters and from around balloons, yet current aspiration catheters do not effectively remove the debris from these interventional devices due to the proximity, or rather lack of proximity, of the aspiration lumen when the aspiration catheter hits the proximal stop of the filter or proximal balloon skirt. Conventional aspiration catheters typically include a guide wire lumen running alongside of a guidewire lumen. The guidewire lumen is typically a short lumen at the distal end of the aspiration catheter, and the distal end of the aspiration lumen extends no farther than the distal end of the guidewire lumen. Therefore, when a widening of the embolic protection filter wire is reached, the aspiration catheter can be advanced no farther. Such a widening may be a strut, a stop or other feature of the embolic protection filter. Such features are commonly found proximal of the filter cavity. This prevents the distal end of the aspiration catheter from entering the filter cavity. However, one cannot extend a fixed aspiration lumen distal of the guide wire lumen without sacrificing the ability of the aspiration catheter to effectively track the guide wire or pass through narrowed body vessels.

What is desirable is a way to get the aspiration lumen distal of such stops and into proximity of the embolic debris to be removed without sacrificing trackability or crossability.

SUMMARY

In a first aspect, there is an intravascular aspirating assembly including an elongate guide wire having a proximally facing filter disposed on a distal portion thereof, a single operator exchange (SOE) aspiration catheter disposed on the guide wire. The aspiration catheter having a proximal end and a distal end, and an aspirating lumen extending therebetween. An extension catheter can be slidably disposed in the aspiration lumen and have a length greater than that of the aspiration catheter, for example. The aspiration catheter can include a guide wire lumen having a distal opening at the distal end of the aspiration catheter and a proximal opening less than 30 cm from the distal opening. The above summary is not intended to describe each disclosed embodiment or every implementation of the invention.

BRIEF DESCRIPTION OF DRAWINGS

The invention may be more completely understood in consideration of the following detailed description of various example embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION OF SELECTED EMBODIMENTS

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
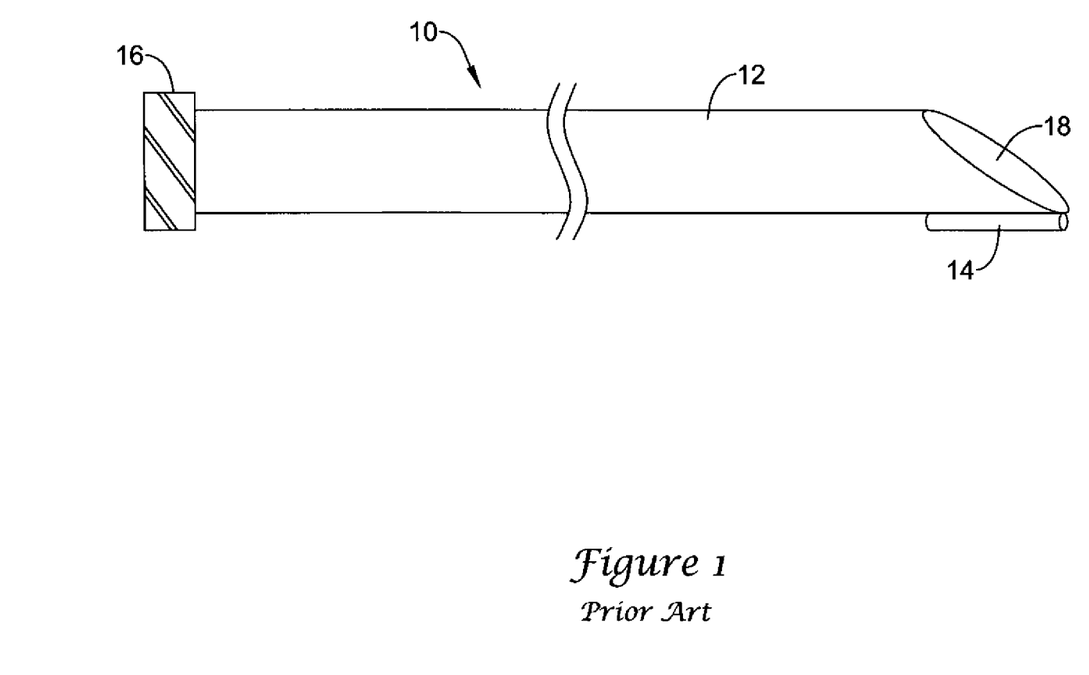
FIG. 1 is a diagrammatic view of a prior art conventional aspiration catheter.

By way of general background, FIG. 1 depicts a conventional single-operator-exchange (SOE) aspiration catheter 10. The catheter includes an aspiration lumen 12 extending from the proximal to the distal end of the catheter and a shorter guidewire lumen 14 disposed at the distal end of the catheter. A luer fitting 16 or other appropriate fitting may be disposed at the proximal end of the catheter. Fitting 16 may be used to connect catheter 10 to a vacuum source such as a syringe to provide aspiration. The aspiration lumen distal opening 18 may be tapered or beveled as shown to ease the movement of catheter 10 distally. This general sketch of a conventional SOE aspiration catheter does not describe all the features of such catheters. Embodiments of the aspiration catheter extension catheter described herein may be used with such a catheter or may be used with a modified aspiration catheter as described in more detail below.

Figure 2:
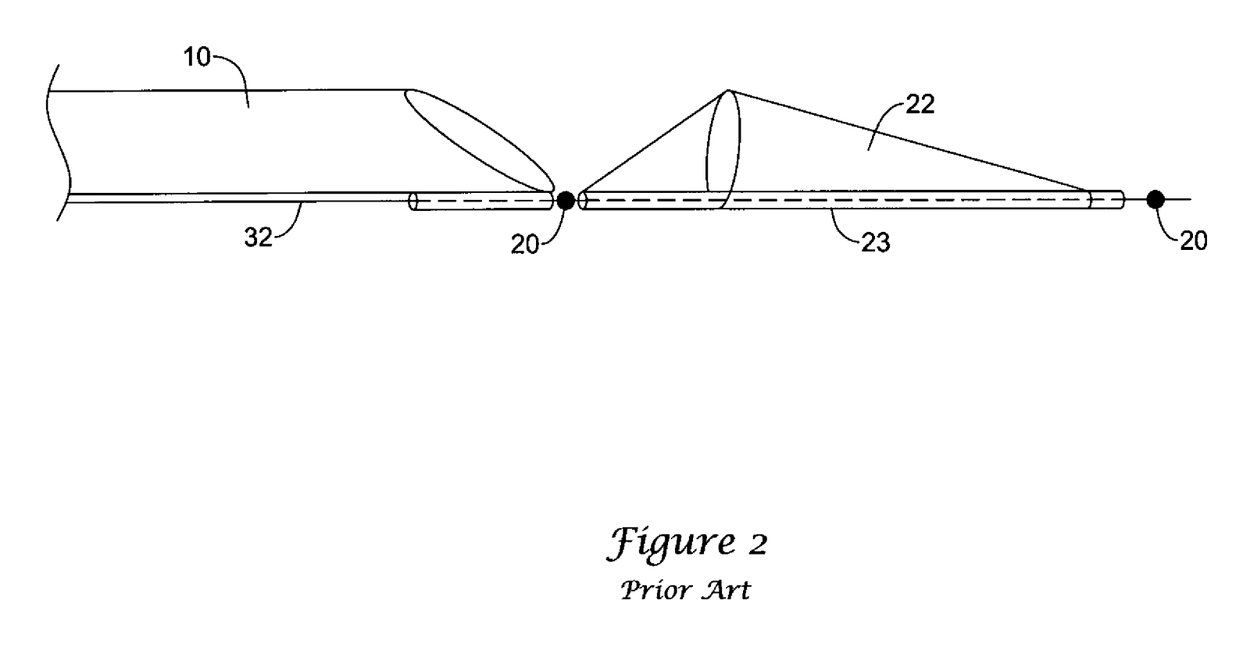
FIG. 2 is a diagrammatic view of the aspiration catheter of FIG. 1 disposed on a filter wire proximate to a distal protection filter.

FIG. 2 depicts the distal portion of such a catheter 10 advanced distally to a proximal stop 20 of an embolic protection filter 22. Embolic protection filter 22 can be disposed on tube 23, which allows filter 22 to rotate about a filter wire 32. The example filter is confined by two stops 20. This example filter is used to illustrate a principle of operation common to many conventional embolic protection filter designs, namely the difficulty or impossibility, when such designs are used with conventional aspiration catheters, of advancing the aspiration catheter aspiration lumen proximate to where the embolic debris collects in the filter cavity. This difficulty is solved by the use of the aspiration catheter extension catheters described herein.

Figure 3:
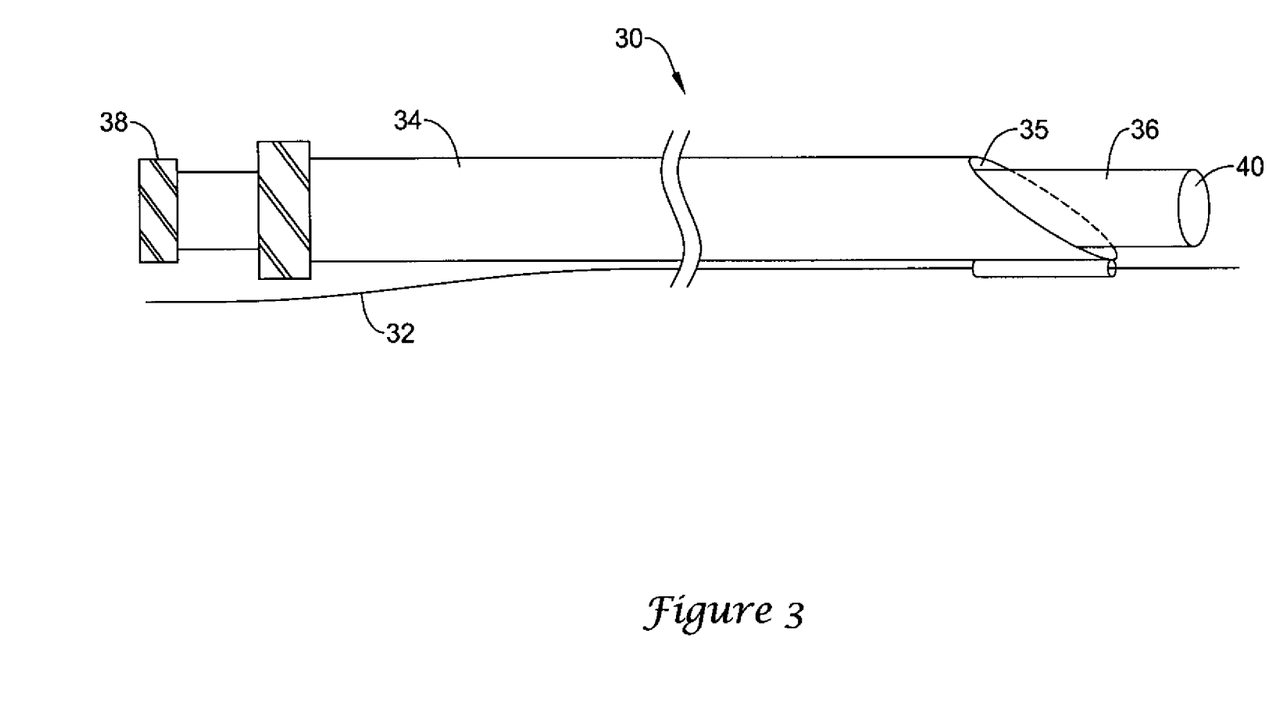
FIG. 3 is a diagrammatic view of a aspiration catheter disposed on a filter wire.

FIG. 3 depicts an aspiration catheter system 30, which is disposed on a filter wire 32 (the embolic protection filter is not shown). This embodiment overcomes the aforementioned difficulty and allows the aspiration lumen distal opening much fuller access to the embolic debris. The system includes an aspiration catheter 34, which may be of the sort described above or may be another suitable aspiration catheter, and an extension catheter 36.

Figure 4:
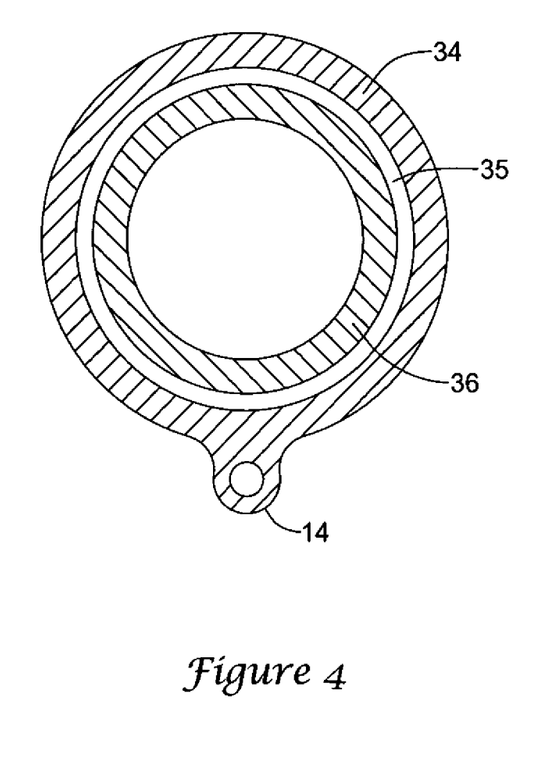
FIG. 4 is a cross-sectional view of the catheter of FIG. 3.

Extension catheter 36 is longer than the aspiration lumen of aspiration catheter 34 and can preferably be freely slid within aspiration catheter 34. Extension catheter tube 36 can be stiffer proximally and more flexibly distally. Such a tube may be fashioned by combining different materials such as stiffer and more flexible polymers and by varying the wall thickness. One contemplated tube includes two polymer layers that extend the length of the tube and provide a constant outer diameter and a constant inner diameter to the tube. One layer is stiffer than the other and the stiffness of tube 36 is varied along its length by varying the thicknesses of the layers while keeping the overall tube thickness constant. The tube profile can match that of the aspiration catheter aspiration lumen and tube 36 can be sized to be as large as possible while allowing it to slide freely within the aspiration lumen, as can be seen most easily with reference to the cross-sectional view of FIG. 4. Extension catheter tube 36 can include a luer fitting 38 at its proximal end for connection to a vacuum source such as a syringe and a distal aspiration lumen opening 40 at its distal end. Extension catheter tube 36 may also include other features such as radiopaque markers at or near its distal end and visible indicia such as stripes at its proximal end so that an operator can discern its position within the vasculature and its position relative to the aspiration catheter 34. Such stripes or other visual indicia permit an operator to know whether and how far distal end 40 of extension catheter tube 36 is extending from an aspiration catheter 34 of known length.

Figure 5:
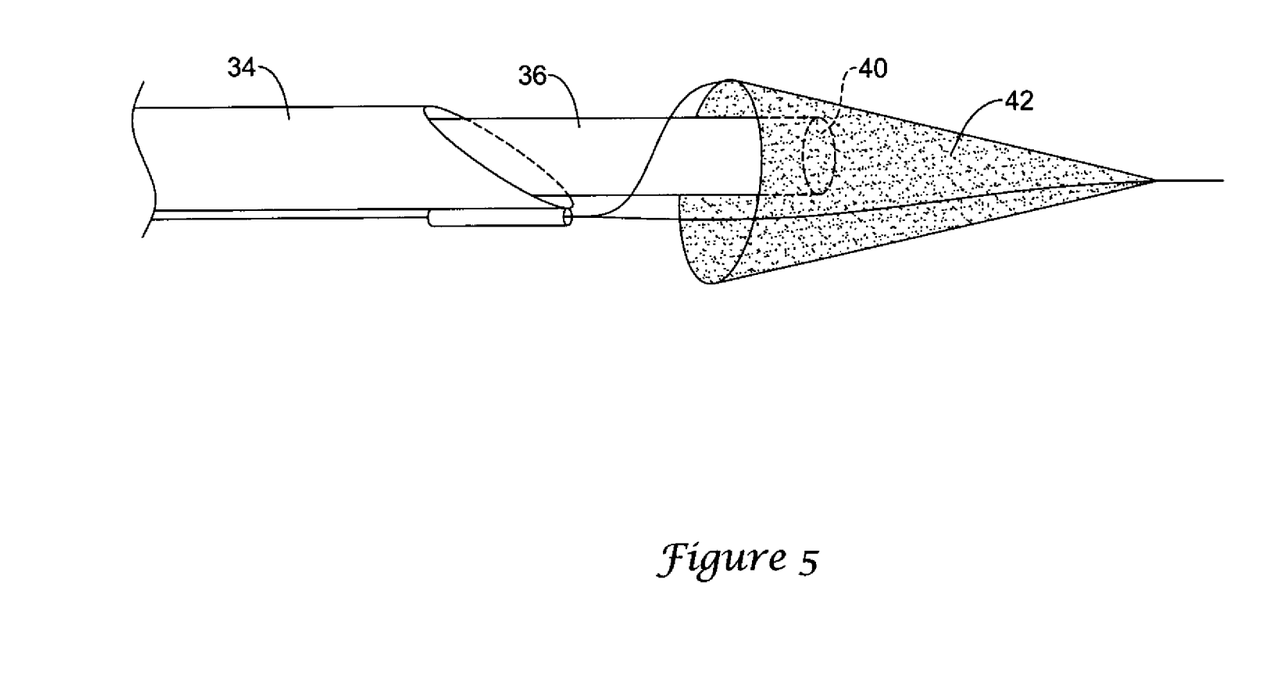
FIG. 5 is a diagrammatic view of the catheter of FIG. 3 in conjunction with a distal protection filter.

The use of system 30 may be better seen with reference to FIG. 5, which depicts the system interacting with an embolic protection filter 42. Generally, when an operator decides to remove embolic debris from filter 22, an aspiration catheter 34 may be advanced distally along the filter wire. Extension catheter 36 may be preloaded within aspiration catheter 34 or may be inserted once the aspiration catheter is in place. While aspiration catheter 34 is being advanced into place, extension catheter tube distal end 40 is fully within the aspiration catheter 34. When aspiration catheter 34 is advanced as far as practicable or desirable (here, the limiting feature is a strut wire of the filter), and is in place, then the extension catheter tube 36 may be advanced through the aspiration catheter into the cavity of the filter 42. Embolic debris may then be aspirated by attaching a syringe to the proximal luer fitting 38 of the extension catheter tube 36 (not shown) and operating the syringe. The aspiration operation may be repeated as desired. If desired, the extension catheter tube 36 may be repositioned farther into the filter cavity prior to repeating the aspiration operation. When the operator is satisfied, extension catheter tube 36 may be retracted into aspiration catheter 34 and both may be retracted from the body, either together or serially. Operation of extension catheter tube 36 may be coordinated with other therapeutic steps as desired. For example, such aspiration may occur after an angioplasty, stent placement or atherectomy operation in some embodiments the distal end includes a chamfer in a single plane extending across substantially the whole width of the distal end. Still further, aspiration catheter 34 may be used without extension catheter tube 36 prior to or subsequent the insertion and use of the catheter 34. Such use may be advantageous for removing larger or more proximally located embolic debris.

Figure 6:
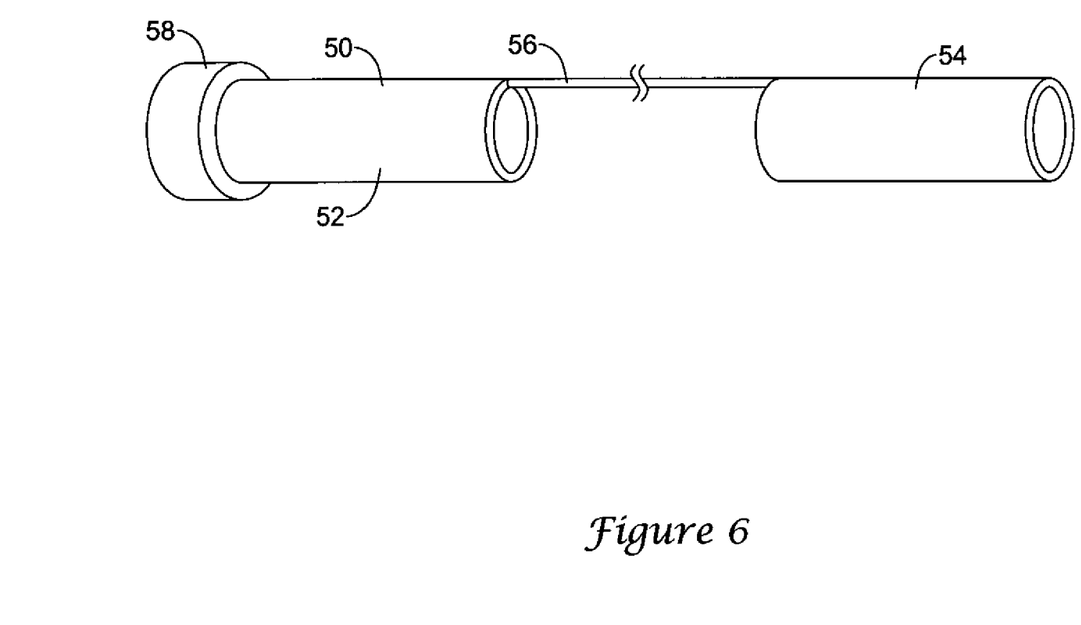
FIG. 6 is a diagrammatic view of another extension catheter tube.

FIG. 6 depicts another extension catheter tube 50, which has two separate tubular sections 52 and 54 connected by a wire 56. In this case, the middle portion of the extension catheter tube 50 is disposed within aspiration catheter lumen 12 during use and the aspiration catheter lumen wall may be made use of. Extension catheter tube 50 includes proximal tubular portion 52 and distal tubular portion 54. A luer fitting 58 can be disposed at the proximal end of the proximal portion 52. Proximal portion 52 may be made from relatively rigid materials and distal portion 54 may be made from relatively flexible materials. Wire 56 may be made from a superelastic material such as Nitinol or metallic material such as stainless steel or any suitable material exhibiting sufficient column strength. A single wire is described in this embodiment but two or more wires distributed symmetrically or asymmetrically along the longitudinal axis or a ribbon-shaped wire would work also.

Figure 7:
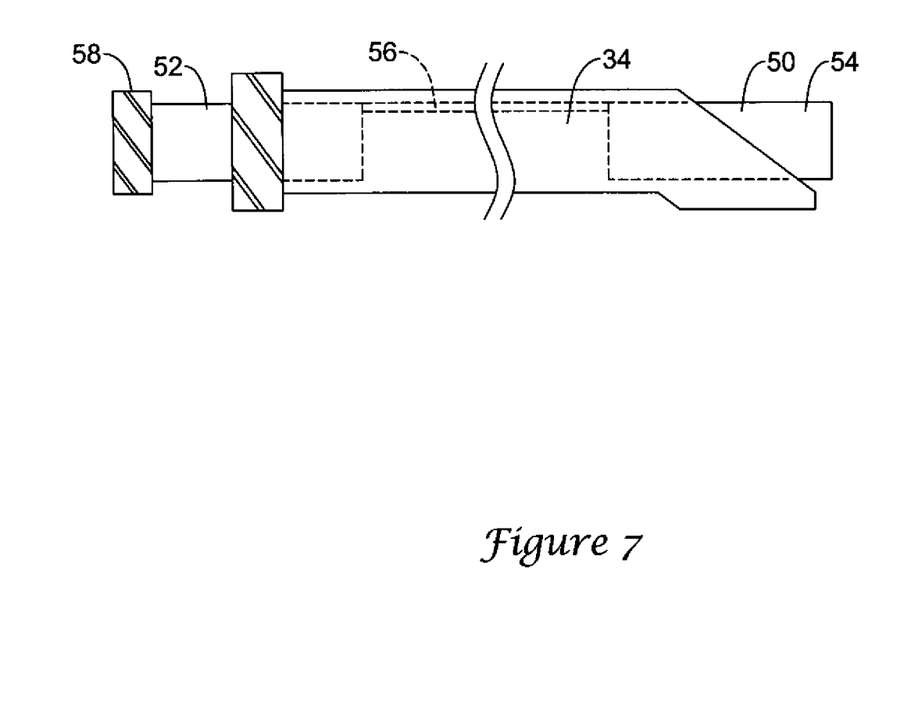
FIG. 7 is a diagrammatic view of the extension catheter tube of FIG. 6 disposed in an aspiration catheter.

Extension catheter tube 50 is shown in an aspiration catheter 34 in FIG. 7. The lengths of proximal and distal tubular portions 52 and 54, and wire portion 56 can be selected so that the distal portion of proximal tubular portion 52 is disposed within aspiration catheter 34 when the distal end of distal tubular portion 54 is near or at the distal end of aspiration catheter 34. The lengths of both the distal and proximal tubular portions 54 and 52, can be selected so that the distal end of catheter tube 50 can be advanced distally from aspiration catheter 34 a desired distance. The desired distance may be, for example, between about 2 and about 6 cm. While there may not be a fluid tight seal between extension catheter tube 50 and aspiration catheter 34, providing a round profile for both aspiration catheter aspiration lumen 35 and extension catheter tube outer surface of similar sizes can provide a substantially sealed fit.

Figure 8:
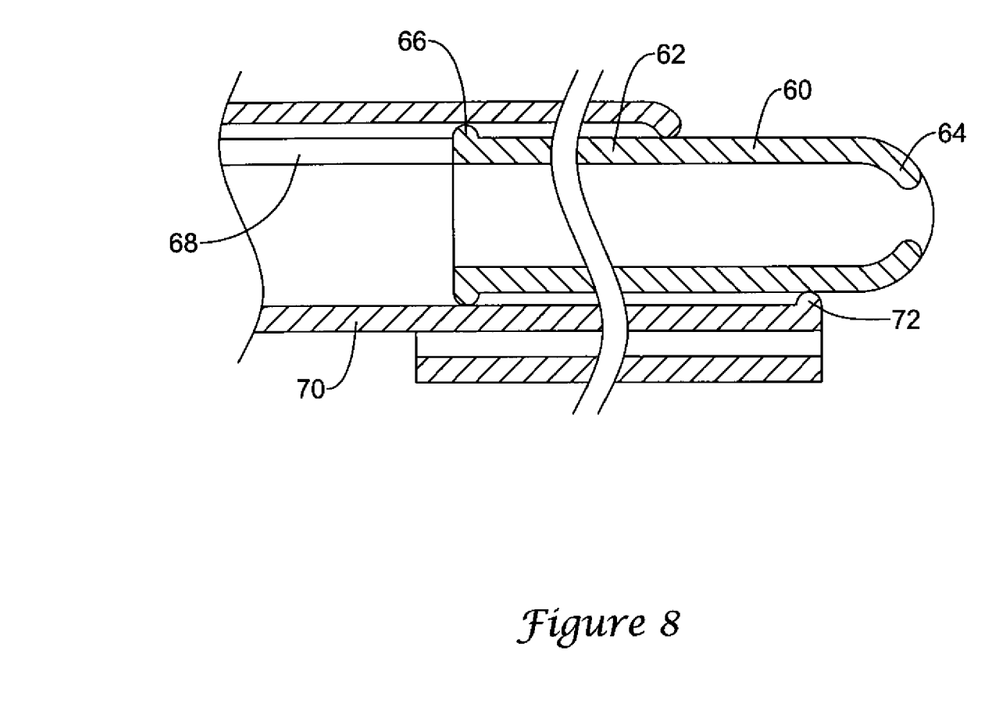
FIG. 8 is a cross-sectional view of the distal portion of an extension catheter tube.

FIG. 8 is a distal cross-sectional view of an extension catheter tube 60 similar to that of FIG. 6. The figure shows a distal tubular portion 62 and a distal portion of a wire 68 that connects distal tubular portion 62 to a proximal tubular portion (not shown). The distal tubular portion 62 includes a tapered distal end 64. Tapered distal end 64 may have the profile shown or may have a beveled or angled profile. And, any of the embodiments described herein may include such a feature at the distal portion of the extension catheter tube. Distal tubular portion 62 also may include one or more circular ridges 66 whose outer profile more closely or exactly matches the inner diameter of the catheter aspiration lumen. Ridge 66 creates a reduced contact area with aspiration catheter 70, which helps with pushability, while also creating a seal between the extension catheter tube 36 and the aspiration catheter 70 to improve aspiration performance.

Aspiration catheter 70 may, as an alternative to ridge(s) 66 on the extension catheter tube 60, include one or more ridges (not shown) on the inner surface of the aspiration lumen. Like the ridges on the extension catheter tube 60, these ridges would reduce the contact between extension catheter tube 60 and aspiration catheter 70 and would seal extension catheter 60 to aspiration catheter 70 to improve aspiration. Aspiration catheter 70 may also include a flexible and elastic lip 72 at the distal opening of the aspiration lumen. Lip 72 can be sized to create a circumferential seal around extension catheter 60. And, versions are contemplated where one or any number of these features are included. For example, a version is contemplated that includes a beveled distal end on the extension catheter and a ridge 66 proximate the proximal end of the distal tubular member. Moreover, it is contemplated that any of these features may be included on any of the catheters and tubes described herein.

Figure 9:
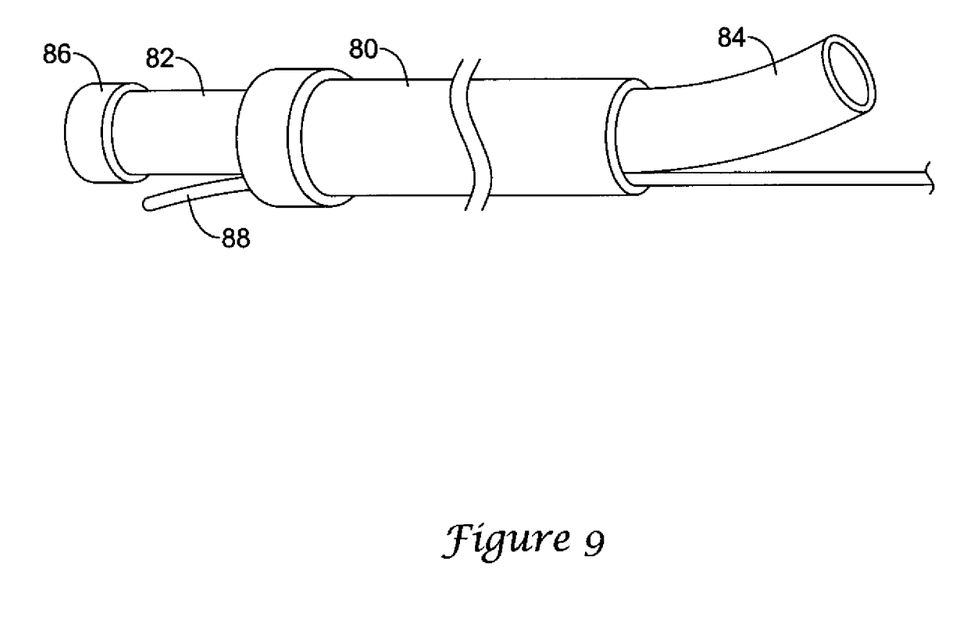
FIG. 9 is a diagrammatic view of another extension catheter tube.
Figure 10:
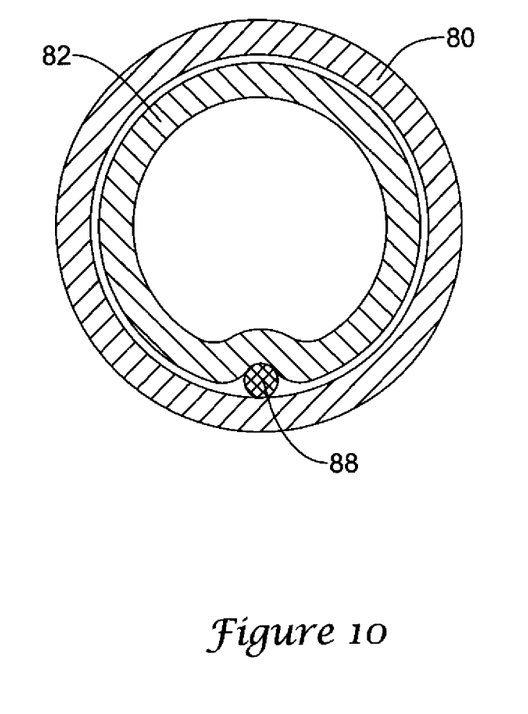
FIG. 10 is a cross-sectional view of the embodiment of FIG. 9.

FIGS. 9 and 10 are diagrammatic and cross-sectional views, respectively, of an extension catheter embodiment tube 82 that works with an over-the-wire aspiration catheter 80, where catheter 80 is advanced over a guide wire 88 by using the lumen of catheter 80. Extension catheter tube 82 is a tubular member of sufficient length to permit distal end 84 to extend out beyond aspiration catheter 80 and includes a luer fitting 86 at its proximal end. The extension catheter 82 is designed to slide into the aspiration catheter 80 alongside the guide wire 88. Because it is desirable to have as large of an aspiration lumen as practicable, the extension catheter tube 82 is configured to resiliently deform around guide wire 88 or other member in the aspiration catheter lumen, as shown in FIG. 10. The wall of extension catheter tube 82 therefore can be partially composed of a compliant or resilient material. Columnar strength, particularly towards the proximal end may be provided for by include longitudinally extending stiffening sections within the wall of the catheter tube 82. These sections may be wires, ribbons, polymeric members or other suitable structure. It may be desirable to vary the stiffness along the length of the extension catheter to provide for more columnar strength towards the proximal end and more flexibility towards the distal end.

Distal end 84 of the extension catheter tube 82 may be shaped so that it curves when free from constraint, as depicted in FIG. 9. This curve may be a simple single arc curve as shown or other curve. For example, the curve may be an ogee curve such that when enough of the distal end is free from constraint, the distal end bends back parallel to but offset from the elongate axis of the greater portion of the extension tube 82. Another contemplated curve is a helical curve so that the distal end portion of the extension catheter may wrap around the guide wire. Including such a curve may make it easier to position the extension catheter in a desired position. For example, with a simple arc curve, the radial displacement of the distal end of the extension catheter tube 82 may be controlled through relative movement of the extension catheter and aspiration catheter 80 and the angular location may be controlled by rotating aspiration catheter 80 and extension catheter tube 82 about the guidewire. This ability to steer aspiration catheter tube 82 independently of the guide wire may be of particular use when the guide wire is fixed in place. Often, a guide wire is fixed because it is a filter wire of an embolic protection filter of the sort that expands in a radially symmetric fashion about the filter wire or the guide wire may be an inflation lumen for an occlusion balloon. Of course, configuring an extension catheter to have a curve as described may be done with any of the embodiments described herein.

Various embodiments of the invention have now been described in detail. Since changes, alterations and additions to the above described embodiments may be made without departing from the nature, spirit or scope of the invention, the invention is not to be limited to the embodiments described above, but rather the scope of the invention is defined only by the appended claims. For example, while the invention is described with respect to intravascular aspiration techniques, the invention is not limited to intravascular devices and methods.

What is claimed is:

1. An intravascular aspirating assembly comprising:
   an elongate guidewire having an occlusion device disposed on a distal portion thereof;
   an aspiration catheter disposed on the guidewire, the aspiration catheter having a proximal end, a distal end and an aspiration lumen extending therebetween; and
   an extension catheter tube slidably disposed in the aspiration lumen, the extension catheter tube having a proximal end, a distal end, a lumen extending therebetween, and a length greater than that of the aspiration catheter,
   wherein the occlusion device is a proximally facing distal protection filter capable of limiting distal travel of the aspiration catheter at a first distal position relative to the guidewire;
   wherein the distal end of the extension catheter tube is capable of advancing to a second distal position distal of the first distal position relative to the guidewire;
   wherein at the second distal position, the extension catheter tube is disposed within the occlusion device; and
   wherein the proximal end of the extension catheter tube extends proximally of the aspiration catheter.

2. The assembly of claim 1, wherein the aspiration catheter further includes a guidewire lumen having a distal opening at the distal end of the aspiration catheter and a proximal opening less than 30 cm from the distal opening.

3. The assembly of claim 1, wherein the extension catheter has a fitting at the proximal end suitable for connection to a syringe.

4. The assembly of claim 1, wherein the extension catheter tube has an outer diameter that is substantially constant along at least 75% of the length of the extension catheter tube and wherein this substantially constant outer diameter terminates no farther than 2 cm from the distal end of the extension catheter tube.

5. The assembly of claim 4, wherein the extension catheter outer diameter is substantially equal to an inner diameter of the aspiration catheter tube that extends along substantially the whole length of the aspiration catheter.

6. The assembly of claim 1, wherein the extension catheter has a tapered distal end.

7. The assembly of claim 6, wherein the tapered distal end includes a chamfer in a single plane extending across substantially the whole width of the distal end.

8. The assembly of claim 6, wherein the tapered distal end is a snub nose.

9. The assembly of claim 1, wherein the extension catheter outer diameter has an outer diameter that is substantially constant and wherein the extension catheter comprises a circumferential ridge having a diameter greater than the outer diameter and disposed on the extension catheter.

10. The assembly of claim 9 wherein the circumferential ridge is proximal of the distal tip of the extension catheter.

11. The assembly of claim 1, further comprising a circumferential ridge disposed in the aspiration lumen.

12. The assembly of claim 1, wherein the extension catheter includes a distal portion that has a non-straight curve when in an unconstrained position.

13. The assembly of claim 12 wherein the curve is a simple arc.

14. The assembly of claim 12 wherein the curve is an ogee curve in a plane that intersects with a longitudinal axis of the aspiration catheter.

15. The assembly of claim 12 wherein the curve is a helical curve.

16. The assembly of claim 1 wherein the extension catheter defines a lumen along the length of the aspiration catheter.

17. The assembly of claim 1 wherein the extension catheter includes a proximal tubular portion and a distal tubular portion both disposed along an elongate axis and spaced apart by a structural member offset from the elongate axis.

18. The assembly of claim 17 wherein the structural member is a wire.

19. The assembly of claim 17 wherein the structural member is a ribbon.

20. An intravascular aspirating assembly comprising:
an elongate guide wire having a proximally facing filter disposed on a distal portion thereof;
an aspirating catheter disposed on the guide wire, the aspirating catheter having a proximal end, a distal end and an aspiration lumen extending therethrough; and
an extension catheter tube disposed in the aspiration lumen and having a length greater than that of the aspiration catheter, the extension catheter tube being discontinuous and including a proximal tubular portion and a distal tubular portion, spaced apart, and connected by a connecting member,
wherein the proximally facing filter is capable of limiting distal travel of the aspiration catheter at a first distal position relative to the guidewire and wherein the distal end of the extension catheter tube is capable of advancing to a second distal position distal of the first distal position relative to the guidewire; and
wherein at the second distal position, the distal end of the extension catheter tube is disposed within the proximally facing filter.

21. The assembly of claim 20, wherein the aspiration catheter further includes a guidewire lumen having a distal opening at the distal end of the aspiration catheter and a proximal opening less than 30 cm from the distal opening.

22. The assembly of claim 20, wherein the extension catheter has a fitting at the proximal end suitable for connection to a syringe.

23. The assembly of claim 20, wherein the extension catheter tube has an outer diameter that is substantially constant along at least 75% of the length of the extension catheter tube and wherein this substantially constant outer diameter terminates no farther than 2 cm from the distal end of the extension catheter tube.

24. The assembly of claim 23, wherein the extension catheter outer diameter is substantially equal to an inner diameter of the aspiration catheter tube that extends along substantially the whole length of the aspiration catheter.

25. The assembly of claim 20, wherein the extension catheter has a tapered distal end.

26. The assembly of claim 25, wherein the tapered distal end includes a chamfer in a single plane extending across substantially the whole width of the distal end.

27. The assembly of claim 25, wherein the tapered distal end is a snub nose.

28. A method of using the assembly of claim 1, comprising the steps of:
inserting an elongate guidewire having an occlusion device disposed on a distal portion thereof;
disposing an aspiration catheter having an aspiration lumen on the guidewire;
slidably disposing an extension catheter which has a length greater than that of the aspiration catheter and which extends proximally of the aspiration catheter in the aspiration lumen;
wherein the occlusion device is a proximally facing distal protection filter capable of limiting distal travel of the aspiration catheter at a first distal position relative to the guidewire;
wherein the distal end of the extension catheter tube is capable of advancing to a second distal position distal of the first distal position relative to the guidewire;
wherein at the second distal position, extension catheter tube is disposed within the occlusion device;
advancing the elongate guidewire intravascularly so that the occlusion device is downstream of a region of interest;
deploying the occlusion device;
performing a therapeutic procedure at the area of interest;
advancing the aspiration catheter to a point proximate the occlusion device;
advancing the extension catheter through the aspiration catheter;
advancing the distal end of the extension catheter past the distal end of the aspiration catheter and into the interior of the occlusion device; and
aspirating embolic debris through the extension catheter.

29. The method of claim 28 wherein the steps of advancing the aspiration catheter and advancing the extension catheter occur simultaneously.

30. The method of claim 28 wherein the step of advancing the extension catheter is subsequent of the step of advancing the aspiration catheter.

31. The method of claim 28 wherein the occlusion device is a proximally facing distal protection filter and wherein the step of advancing the distal end of the extension catheter includes advancing the distal end of the extension catheter into the distal protection filter.

32. The method of claim 28 wherein the step of advancing the aspiration catheter includes the step of advancing the aspiration catheter distal end past the region of interest.

\* \* \* \* \*

UNITED STATES PATENT AND TRADEMARK OFFICE
CERTIFICATE OF CORRECTION

| | |
|---|---|
| PATENT NO. | : 8,465,456 B2 |
| APPLICATION NO. | : 12/183388 |
| DATED | : June 18, 2013 |
| INVENTOR(S) | : Timothy Stivland |

It is certified that error appears in the above-identified patent and that said Letters Patent is hereby corrected as shown below:

In the Specification:

Column 1, Line 34: delete "a guidewire" and insert -- an aspiration --.

Column 5, Line 5: delete "profile shown" and insert -- snub nose profile shown --.

Signed and Sealed this
Third Day of September, 2013

Teresa Stanek Rea
*Acting Director of the United States Patent and Trademark Office*